United States Patent
Smith et al.

(10) Patent No.: US 7,879,275 B2
(45) Date of Patent: *Feb. 1, 2011

(54) ORTHOPAEDIC BEARING AND METHOD FOR MAKING THE SAME

(75) Inventors: Todd S. Smith, Fort Wayne, IN (US); Mark D. Hanes, Winona Lake, IN (US); Richard King, Warsaw, IN (US)

(73) Assignee: DePuy Products, Inc., Warsaw, IN (US)

( * ) Notice: Subject to any disclaimer, the term of this patent is extended or adjusted under 35 U.S.C. 154(b) by 1093 days.

This patent is subject to a terminal disclaimer.

(21) Appl. No.: 11/027,662

(22) Filed: Dec. 30, 2004

(65) Prior Publication Data

US 2006/0149388 A1 Jul. 6, 2006

(51) Int. Cl.
*B29C 43/20* (2006.01)

(52) U.S. Cl. .................. 264/248; 264/250; 264/254; 264/320; 264/275; 264/267; 264/266

(58) Field of Classification Search .............. None
See application file for complete search history.

(56) References Cited

U.S. PATENT DOCUMENTS

| | | | |
|---|---|---|---|
| 2,948,666 A | 11/1956 | Lawton | |
| 3,297,641 A | 1/1967 | Werber et al. | |
| 3,352,818 A | 11/1967 | Meyer et al. | |
| 3,646,155 A | 2/1972 | Scott | 260/827 |
| 3,671,477 A | 6/1972 | Nesbitt | 524/424 |
| 3,758,273 A | 9/1973 | Johnston et al. | |
| 3,787,900 A | 1/1974 | McGee | |
| 3,944,536 A | 3/1976 | Lupton et al. | |
| 3,997,512 A | 12/1976 | Casey et al. | |
| 4,055,862 A | 11/1977 | Farling | |
| 4,138,382 A | 2/1979 | Polmanteer | 523/113 |
| 4,181,983 A | 1/1980 | Kulkarni | |
| 4,195,366 A | 4/1980 | Jarcho et al. | |
| 4,281,420 A | 8/1981 | Raab | |
| 4,322,398 A | 3/1982 | Reiner et al. | |
| 4,330,514 A | 5/1982 | Nagai et al. | |
| 4,366,618 A | 1/1983 | Lakes | |
| 4,373,217 A | 2/1983 | Draenert | |
| 4,390,666 A | 6/1983 | Moriguchi et al. | 525/194 |
| 4,452,973 A | 6/1984 | Casey et al. | |
| 4,481,353 A | 11/1984 | Nyilas et al. | |

(Continued)

FOREIGN PATENT DOCUMENTS

BE  A-1001574  12/1989

(Continued)

OTHER PUBLICATIONS

"Poly Two Carbon-Polyethylene Composite-A Carbon Fiber Reinforced Molded Ultra-High Molecular Weight Polyethylene", Technical Report, Zimmer (a Bristol-Myers Squibb Company), Warsaw (1977).

(Continued)

*Primary Examiner*—Edmund H. Lee
(74) *Attorney, Agent, or Firm*—Barnes & Thornburg LLP

(57) ABSTRACT

An orthopaedic bearing includes a ceramic component having a polymer composite secured thereto. A method of making an orthopaedic bearing is also disclosed.

23 Claims, 2 Drawing Sheets

U.S. PATENT DOCUMENTS

| | | | |
|---|---|---|---|
| 4,483,333 A | 11/1984 | Wartman | 128/90 |
| 4,518,552 A | 5/1985 | Matsuo et al. | 264/524 |
| 4,539,374 A | 9/1985 | Fenton et al. | 525/240 |
| 4,563,489 A | 1/1986 | Urist | |
| 4,578,384 A | 3/1986 | Hollinger | |
| 4,582,656 A | 4/1986 | Hoffmann | |
| 4,586,995 A | 5/1986 | Randall et al. | |
| 4,637,931 A | 1/1987 | Schmitz | |
| 4,655,769 A | 4/1987 | Zachariades | |
| 4,668,527 A | 5/1987 | Fujita et al. | 427/35 |
| 4,743,493 A | 5/1988 | Sioshansi et al. | |
| 4,747,990 A | 5/1988 | Gaussens et al. | |
| 4,816,517 A | 3/1989 | Wilkus et al. | 524/520 |
| 4,843,112 A | 6/1989 | Gerhart et al. | |
| 4,876,049 A | 10/1989 | Aoyama et al. | |
| 4,880,610 A | 11/1989 | Constantz | |
| 4,888,369 A | 12/1989 | Moore, Jr. | 524/522 |
| 4,902,460 A | 2/1990 | Yagi | 264/83 |
| 4,944,974 A | 7/1990 | Zachariades | |
| 5,001,206 A | 3/1991 | Bashir et al. | |
| 5,014,494 A | 5/1991 | George | |
| 5,024,670 A | 6/1991 | Smith et al. | |
| 5,037,928 A | 8/1991 | Li et al. | |
| 5,053,312 A | 10/1991 | Takeda | |
| 5,084,051 A | 1/1992 | Tormala et al. | |
| 5,085,861 A | 2/1992 | Gerhart et al. | |
| 5,130,376 A | 7/1992 | Shih | 525/240 |
| 5,133,757 A | 7/1992 | Sioshansi et al. | 623/18 |
| 5,137,688 A | 8/1992 | DeRudder | |
| 5,149,368 A | 9/1992 | Liu et al. | |
| 5,153,039 A | 10/1992 | Porter et al. | |
| 5,160,464 A | 11/1992 | Ward et al. | |
| 5,160,472 A | 11/1992 | Zachariades | |
| 5,180,394 A | 1/1993 | Davidson | 623/18 |
| 5,192,323 A | 3/1993 | Shetty et al. | 623/16 |
| 5,200,439 A | 4/1993 | Asanuma | |
| 5,210,130 A | 5/1993 | Howard, Jr. | |
| 5,236,563 A | 8/1993 | Loh | |
| 5,264,214 A | 11/1993 | Rhee et al. | |
| 5,314,478 A | 5/1994 | Oka et al. | |
| 5,356,998 A | 10/1994 | Hobes | |
| 5,385,887 A | 1/1995 | Yim et al. | |
| 5,407,623 A | 4/1995 | Zachariades et al. | |
| 5,414,049 A | 5/1995 | Sun et al. | 525/333.7 |
| 5,439,949 A | 8/1995 | Lucas et al. | |
| 5,449,745 A | 9/1995 | Sun et al. | 528/483 |
| 5,466,530 A | 11/1995 | England et al. | |
| 5,478,906 A | 12/1995 | Howard, Jr. | |
| 5,480,683 A | 1/1996 | Chabrol et al. | |
| 5,492,697 A | 2/1996 | Boyan et al. | |
| 5,508,319 A | 4/1996 | DeNicola | 526/352 |
| 5,515,590 A | 5/1996 | Pienkowski | |
| 5,543,471 A | 8/1996 | Sun et al. | |
| 5,549,698 A | 8/1996 | Averill et al. | |
| 5,549,700 A | 8/1996 | Graham et al. | |
| 5,577,368 A | 11/1996 | Hamilton et al. | |
| 5,593,719 A | 1/1997 | Dearnaley et al. | 427/2.26 |
| 5,607,518 A | 3/1997 | Hoffman et al. | |
| 5,609,638 A | 3/1997 | Price et al. | 623/18 |
| 5,639,280 A | 6/1997 | Warner et al. | |
| 5,645,594 A | 7/1997 | Devanathan et al. | |
| 5,645,882 A | 7/1997 | Llanos | 427/2.24 |
| 5,650,485 A | 7/1997 | Sun et al. | |
| 5,674,293 A | 10/1997 | Armini et al. | 623/16 |
| 5,684,124 A | 11/1997 | Howard, Jr. et al. | |
| 5,702,448 A | 12/1997 | Buechel et al. | 623/16 |
| 5,702,456 A | 12/1997 | Pienkowski | 623/18 |
| 5,709,020 A | 1/1998 | Pienkowski et al. | |
| 5,728,748 A | 3/1998 | Sun et al. | |
| 5,753,182 A | 5/1998 | Higgins | |
| 5,876,453 A | 3/1999 | Beaty | 623/16 |
| 5,879,387 A * | 3/1999 | Jones et al. | 623/18.11 |
| 5,879,388 A | 3/1999 | Pienkowski et al. | 623/18 |
| 5,879,400 A | 3/1999 | Merrill et al. | 623/22 |
| 5,879,404 A | 3/1999 | Bateman et al. | |
| 5,879,407 A | 3/1999 | Waggener | 623/22 |
| 5,947,893 A | 9/1999 | Agrawal et al. | |
| 6,005,053 A | 12/1999 | Parikh et al. | |
| 6,017,975 A | 1/2000 | Saum et al. | |
| 6,027,742 A | 2/2000 | Lee et al. | |
| 6,087,553 A | 7/2000 | Cohen et al. | |
| 6,136,029 A | 10/2000 | Johnson et al. | |
| 6,139,322 A | 10/2000 | Liu | |
| 6,139,585 A | 10/2000 | Li | |
| 6,143,232 A | 11/2000 | Rohr | |
| 6,162,225 A | 12/2000 | Gertzman et al. | |
| 6,165,220 A * | 12/2000 | McKellop et al. | 128/898 |
| 6,168,626 B1 | 1/2001 | Hyon et al. | |
| 6,228,900 B1 | 5/2001 | Shen et al. | |
| 6,242,507 B1 | 6/2001 | Saum et al. | |
| 6,245,276 B1 | 6/2001 | McNulty et al. | |
| 6,281,262 B1 | 8/2001 | Shikinami | |
| 6,281,264 B1 | 8/2001 | Salovey et al. | |
| 6,296,667 B1 | 10/2001 | Johnson et al. | |
| 6,302,913 B1 | 10/2001 | Ripamonti et al. | |
| 6,316,158 B1 | 11/2001 | Saum et al. | |
| 6,331,312 B1 | 12/2001 | Lee et al. | |
| 6,365,089 B1 | 4/2002 | Krebs et al. | |
| 6,376,573 B1 | 4/2002 | White et al. | |
| 6,414,086 B1 | 7/2002 | Wang et al. | |
| 6,494,917 B1 | 12/2002 | McKellop et al. | |
| 6,652,943 B2 | 11/2003 | Tukachinsky et al. | |
| 6,976,999 B2 * | 12/2005 | Charlebois et al. | 623/16.11 |
| 2002/0006428 A1 | 1/2002 | Mahmood et al. | |
| 2003/0144741 A1* | 7/2003 | King et al. | 623/23.58 |
| 2003/0144742 A1* | 7/2003 | King et al. | 623/23.58 |

FOREIGN PATENT DOCUMENTS

| | | |
|---|---|---|
| DE | 196 10715 C1 | 6/1997 |
| EP | 0 169 259 | 7/1984 |
| EP | 0 373 800 A1 | 6/1990 |
| EP | 0 395 187 A2 | 10/1990 |
| EP | 0 505 634 | 9/1992 |
| EP | 0722973 A1 | 7/1996 |
| EP | 0729981 A1 | 9/1996 |
| EP | 0 737481 A1 | 10/1996 |
| EP | 0 803 234 A1 | 10/1997 |
| EP | 0 963 824 A2 | 12/1999 |
| EP | 0 963 824 A3 | 9/2001 |
| EP | 1 277 450 A2 | 1/2003 |
| EP | 1421918 A1 | 5/2004 |
| JP | 58-157830 A | 9/1983 |
| JP | A-59 168 050 | 9/1984 |
| JP | A-62 243 634 | 1/1987 |
| JP | 04-198242 | 7/1992 |
| JP | A-04 185 651 | 7/1992 |
| JP | 09 12 22 22 | 5/1997 |
| WO | WO 93/10953 | 11/1991 |
| WO | WO 95/21212 | 8/1995 |
| WO | WO 96/09330 | 3/1996 |
| WO | WO 97/29793 | 8/1997 |
| WO | WO 98/01085 | 1/1998 |
| WO | WO 98/14223 | 4/1998 |
| WO | WO 98/29145 | 7/1998 |

OTHER PUBLICATIONS

Atkinson, J.R. et al., "Silane cross-linked polyethylene for prosthetic applications. Part I. Certain physical and mechanical properties related to the nature of the material", Biomaterials, 4:267 (1983).

Atkinson, J.R. et al., "Silane cross-linked polyethylene for prosthetic applications. Part II. Creep and wear behavior and a preliminary moulding test", Biomaterials, 5:326 (1984).

Bartel, D.L. et al., "The Effect of Comformity, Thickness, and Material on Stresses in Ultra-High Molecular Weight Components for Total Hip Replacement", J. Bone & Joint Surgery. 68-A(7):1041 (1986).

Bhateja, S.K., "Radiation-Induced Crystallinity Changes In Pressure-Crystallized Ultra-High Molecular Weight Polyethylene", J. Macromol. Sci. Phys., B22(1): 159 (1983).

Bhateja, S.K. et al., "Radiation-Induced Crystallinity Changes in Linear Polyethylene", J. Polym. Sci. Polym. Phys. Ed., 21: 523 (1983).

Bhateja, S.K. et al., "Radiation-Induced Crystallinity Changes in Polyethylene Blends", J. Mater. Sci., 20: 2839 (1985).

Birkinshaw, C. et al., "The Melting Behavior of Irradiated Polymers", Thermochimica Acta, 117: 365 (1987).

Bloebaum, R.D. et al., "Investigation of Early Surface Delamination Observed in Retrieved Heat-Pressed Tibial Inserts", Clin. Orthop., 269: 120 (1991).

Bremmer, T. et al., "Peroxide Modification of Linear Low-Density Polyethylene: A Comparison of Dialkyl Peroxides", J. Appl. Polym. Sci., 49 : 785 (1993).

Brown, K. J. et al., "The Wear of Ultra-High Molecular Weight Polyethylene with Reference to Its Use in Prostheses", Plastics in Medicine & Surgery Plastics & Rubber Institute, London, 2.1 (1975).

Chen, C.J. et al., "Radiation-Induced crosslinking: II. Effect on the crystalline and amorphous densities of polyethylene", Coll. & Polym. Sci.,269: 469 (1991).

Chen, Y.L. et al., "Photocrosslinking of Polyethylene I. Photoinitiators, Crosslinking Agent, and Reaction Kinetics", J. Polym. Sci., Part A: Polym. Chem. 27: 4051 (1989).

Chen, Y.L. et al., "Photocrosslinking of Polyethylene. II. Properties of Photocrosslinked Polyethylene", J. Polym. Sci., Part A; Polym. Chem., 27: 4077 (1989).

Connelly, G.M. et al., "Fatigue Crack Propagation Behavior of Ultrahigh Molecular Weight Polyethylene", J. Orthop. Res., 2: 119 (1984).

deBoer, A.P. et al., "Polyethylene Networks Crosslinked in Solution: Preparation, Elastic Behavior, and Oriented Crystallization. I. Crosslinking In Solution", J. Polym. Sci., Polym. Phys. Ed., 14: 187 (1976).

deBoer, J. et al., "Crosslinking of Ultra-High Molecular Weight Polyethylene in the Melt by Means of 2,5-dimethyl-2,5-bis (tert-butyldioxy)-3-hexyne", Makromol. Chem. Rapid Commun., 2: 749 (1981).

deBoer, J. et al., "Crosslinking of Ultra-High Molecular Weight Polyethylene in the Melt by Means of 2,5-dimethyl-2,5-bis (tert-butyldioxy)-3-hexyne: 2. Crystallization Behavior and Mechanical Properties", Polymer, 23: 1944 (1982).

deBoer, J. et al., "Crosslinking of Ultra-High Molecular Weight Polyethylene in the Oriented State with Dicumylperoxide", Polymer, 25: 513 (1984).

Dijkstra, D.J. et al., "Cross-linking of ultra-high molecular weight polyethylene in the melt by means of electron bean irradiation", Polymer, 30: 866 (1989).

Ding Z.Y. et al., "Model Filled Polymers. VI. Determination of the Crosslink Density of Polymeric Beads by Swelling," J. Polym. Sci., Part B: Poly. Phys., 29: 1035 (1991).

Eyerer, P. et al., "Property changes of UHMW polyethylene hip cup endoprostheses during implantation", J. Biomed. Materials Res., 18: 1137 (1984).

Eyerer, P., "Polyethylene", Concise Encyclopedia of Medical and Dental Implant Materials, Pergamon Press, Oxford, 271 (1990).

Ferris, B.D., "A quantitiative study of the tissue reaction and its relationship to debris production from a joint implant", J. Exp. Path., 71: 367 (1990).

Gielenz G. et al., "Crystalline and supermolecular structures in linear polyethylene irradiated with fast electrons", Colloid & Polymer Sci., 260: 742 (1982).

Grobbelaar, C.J. et al., "The Radiaion improvement of Polyethylene Prosthesis", J. Bone & Joint Surgery, 60-B(3): 370-374 (1978).

Goodman, S. et al., "Polyethylene wear in knee arthroplasty", Acta Orthop. Scand., 63(3): 358 (1992).

Grood, E.S. et al., "Analysis of retrieved implants: Crystallinity changes in ultrahigh molecular weight polyethylene", J. Biomedical Materials Res., 16: 399 (1982).

Huang, D.D. et al., "Cyclic Fatigue Behaviors of UHMWPE and Enhanced UHMWPE", Trans. $38^{th}$ Ann. Mtg., Orthop. Res. Soc., 403 (1992).

Kamel, I. et al., "A Model for Radiation-Induced Changes in Ultrahigh-Molecular-Weight-Polyethylene", J. Polym. Sci., Polym. Phys. Ed., 23:2407 (1985).

Kampouris, E.M. et al., "Benzyl Peroxide as a Crosslinking Agent for Polyethylene", J. Appl. Polym. Sci., 34: 1209 (1987).

Kao, Y.H., "Crystallinity in chemically crosslinked low density polyethylenes: 1 Structural and fusion studies", Polymer, 27: 1669 (1986).

Katq, K. et al., "Structural Changes and Melting Behavior of γ-Irradiated Polyethylene", Japanese J. Appl. Phys., 20: 691 (1981).

Kunert, K.A. et al., "Structural investigation of chemically crosslinked low density polyethylene", Polymer, 22: 1355 (1981).

Kurth, M. et al., "Effects of Radiation Sterilization on UHMW-Polyethylene", Trans. Third World Biomaterials Congress, 589 (1988).

Landy, M.M. et al., "Wear of Ultra-high-molecular-weight Polyethylene Components of 90 Retrieved Knee Prostheses", Arthroplasty, Supplement, 3: S73 (1988).

Lem, K. et al., "Rheological Properties of Polyethylenes Modified with Dicumyl Peroxide", J. Appl. Polym. Sci., 27: 1367 (1982).

Li, S. et al., "Characterization and Description of an Enhanced Ultra High Molecular Weight Polyethylene for Orthopaedic Bearing Surfaces", Trans. $16^{th}$ Ann. Soc. Biomaterials Meeting, Charleston, SC, 190 (1990).

Manley, T.R. et al., "The effects of varying peroxide concentration in crosslinked linear polyethylene", Polymer, 12:176 (1971).

McKellop, H. et al., "Friction, Lubrication and Wear of Polyethylene Metal and Polyethylene/Ceramic Hip Prostheses on a Joint Simulator", Fourth World Biomaterials Congress, Berlin, April., 118 (1992).

Minkova, L., "DSC of γ-irradiated ultra-high molecular weight polyethylene and high density polyethylene of normal molecular weight", Colloid & Polymer Sci., 266: 6 (1988).

Minkova, L. et al., "Blends of normal high density and ultra-high molecular weight polyethylene, γ-irradiated at a low dose", Colloid & Polymer Sci., 268: 1018 (1990).

Nagy, E.V. et al., "A Fourier transform infrared technique for the evaluation of polyethylene orthopaedic bearing materials", Trans. $16^{th}$ Ann. Soc. For Biomaterials Meeting, Charleston, SC 109 (1990).

Narkis, M. et al., "Structure and Tensile Behavior of Irradiation-and Peroxide-Crosslinked Polyethylene", J. Macromol. Sci.-Phys., B26(1): 37 (1987).

Nusbaum, H. J. et al., "The Effects of Radiation Sterilization on the Properties of Ultrahigh Molecular Weight Polyethylene", J. Biomed. Materials Res., 13: 557 (1979).

Oonishi, H. et al., "Improvement of Polyethylene by Irradiation in Artificial Joints", Radiat, Phys. Chem., 39: 495 (1992).

Oonishi, H. et al., "In Vivo and In Vitro Wear Behavior on Weightbearing Surfaces of Polyethylene Sockets Improved by Irradiation in Total Hip Prostheses", Surface Modification Technologies V, 101-115 (1992), Sudarsahn T.S. et al., ed. The Institute of Materials.

Painter, P.C., et al., "The Theory of Vibrational Spectroscopy and its Application to Polymeric Materials", Ed. John Wiley & Sons, New York, U.S.A., (1982).

Paul, J. P., "Forces Transmitted by Joints in the Human Body", Proc. Instn. Mech. Engrs. 181, Part 3J, Paper 8 (1966).

Qu, B.J. et al., "Photocross-linking of Low Density Polyethylene. I Kinetics and Reaction Parameters", J. Appl. Polym. Sci., 48: 701 (1993).

Qu, B.J. et al., "Photocross-linking of Low Density Polyethylene. II Structure and Morphology", J. Appl. Polym. Sci., 48: 711 (1993).

Rimnac, C.M. et al., "Chemical and Mechanical Degradation of UHMWPE: Report of the Development of an In vitro Test", J. Appl. Biomaterials, 5:17 (1994).

Rimnac, C.M. et al., "Observations of Surface Damage and Degradation on Retrieved PCA Knee Implants", Trans. $38^{th}$ Ann. Orthopaedic Res. Society, Washington, D.C., 330 (1992).

Rimnac, C.M. et al., "Post-Irradiation Aging of Ultra-High Molecular Weight Polyethylene", J. Bone & Joint Surgery, 76-A(7): 1052 (1994).

Roe, R. et al., "Effect of radiation sterilization and aging on ultrahigh molecular weight polyethylene", J. Biomed. Mat. Res., 15: 209 (1981).

Rose, R.M. et al., "On the True Wear Rate of Ultra-High Molecular Weight Polyethylene in the Total Hip Prosthesis", J. Bone & Joint Surgery, 62A(4): 537(1980).

Rose, R.M. et al., "Exploratory Investigations in the Structure Dependence of the Wear Resistance of Polyethylene", Wear, 77:89 (1982).

Rostoker, W. et al., "The Appearances of Wear on Polyethylene—A Comparison of in vivo and in vitro Wear Surfaces", J. Biomed. Materials Res., 12:317 (1978).

Seedhom, B.B. et al., "Wear of Solid Phase Formed High Density Polyethylene in Relation to the Life of Artificial Hips and Knees", Wear, 24: 35 (1973).

Shen, C. et al., "The Friction and Wear Behavior of Irradiated Very High Molecular Weight Polyethylene", Wear, 30:349 (1974).

Shinde, A. et al., "Irradiation of Ultrahigh-Molecular-Weight Polyethylene", J. Polym. Sci., Polym. Phys. Ed., 23: 1681 (1985).

Spruiell, J.E. et al., "Methods of Experimental Physics", L. Marton & C. Marton, Eds., vol. 16, Part B Academic Press, New York (1980).

Streicher, R.M., "Ionizing irradiation for sterilization and modification of high molecular weight polyethylenes" Plastics & Rubber Processing & Applications, 10: 221 (1988).

Streicher, R.M., "Investigation on Sterilization and Modification of High Molecular Weight Polyethylenes by Ionizing Irradiation", Beta-gamma, 1/89:34-43.

Swanson, S.A.V. et al., "Chapter 3, Friction, Lubrication and Wear", The Scientific Basis of Joint Replacement, Pittman Medical Publishing Co., Ltd. (1977).

Wang, X. et al., "Melting of Ultrahigh Molecular Weight Polyethylene", J. App. Polymer Sci., 34:593 (1987).

Wright, T.M. et al., "The effect of carbon fiber reinforcement on contact area, contact pressure, and time-dependent deformation in polyethylene tibial components", J. Biomed. Materials Res., 15:719 (1981).

Zachariades, A.E., "A New Class of UHMWPE Orthopaedic Prosthetic Devices with Enhanced Mechanical Properties", Trans. Fourth World Biomaterials Congress, Berlin 623 (1992).

Zhao, Y. et al., "Effect of Irradiation on Crystallinity and Mechanical Properties of Ultrahigh Molecular Weight Polyethylene", J. Appl. Polym. Sci., 50:1797 (1993).

"News You Can Use", vol. II, No. 2 (May 1996).

"For the Tough Jobs: 1900 UHMW Polymer", Himont, Inc. (1988).

"Abrasion-Resistant 1900 UHMW Polymer", Hercules, Inc. (1979).

"Technical Information: 1900 Ultrahigh Molecular Weight Polymer, General Information and Applications", Bulletin JPE-101A, Hercules, U.S.A., Inc., (1989).

"Technical Information: 1900 Ultrahigh Molecular Weight Polymer, Nuclear Radiation Effects", Bulletin HPE-111, Himont U.S.A., Inc. (1985).

"Technical Information: 1900 Ultrahigh Molecular Weight Polymer, Effect of Polymer Modification", Bulletin HPE-116, Himont U.S.A., Inc. (1987).

"Ultra-High Molecular Weight Polyethylene as Biomaterial in Orthopaedic Surgery", Hogrefe & Huber Publishers.

Appleby, R.W. et al., "Post-gamma irradiation cross-linking of polyethylene tape by acetylene treatment", J. Material Sci., 29: 227-231 (1994).

Higgins, J.C. et al., "Evaluation of Free Radical Reduction Treatments for UHMWPE", Proceedings of the 42$^{nd}$ Annual Mtg., Orthopaedic Res. Soc., Feb. 19-22:485(1996).

Jasty, M. et al., "Marked Improvement in the Wear Resistance of a New Form of UHMPWE in a Physiologic Hip Simulator", Trans. 43$^{rd}$ Ann. Mtg., Orthopaedic Research Soc., San Francisco, CA, Feb. 9-12:785(1997).

Jasty, M. et al., "Marked Improvement in the Wear Resistance of a New Form of UHMPWE in a Physiologic Hip Simulator", Trans. Soc. Biomaterials, vol. XX, p. 71, 23$^{rd}$ Ann. Mtg. Soc. for Biomaterials. New Orleans, Louisana, U.S.A., Apr. 30-May 4:157 (1997).

Streicher, Influence of Ionizing Irradiation in Air and Nitrogen for Sterilization of Surgical Grade Polyethylene for Implants, Radiat. Phys. Chem., vol. 31, Nos. 4-6: 693-698 (1988).

Pleiss et al., "The Improvement of Polyethylene Prostheses Through Radiation Crosslinking", Radiat.. Phys. Chem., 9: 647-652 (1977).

Streicher, "The Behavior of UHMW-PE when Subjected to Sterilization by Ionizing Radiation", Ultra-High Molecular Weight Polyethylene as Biomaterial in Orthopedic Surgery, 66-73 (1990).

Saunders, C. et al., "Radiation Effects on Microorganisms and Polymers for Medical Products", Medical Device & Diagnostic Industry, 222:89-22 (1993).

Kang et al., "The Radiation Chemistry of Polyethylene IX. Temperature Coefficient of Cross-linking and Other Effects", J. Amer. Chem. Society, 89(9): 1980-1986 (1967).

Rose et al., "Radiation Sterilization and the Wear Rate of Polyethylene", J. Orthopaedic Res. Society, 2(4): 393-400 (1984).

Oonishi, H. et al., "Super Low Wear Cross-Linked UHMWPE by Heavy High-Dose Gamma Radiation", WPOA 2$^{nd}$ Congress of Hip Section, 61 (1996).

Jahan et al., "Combined chemical and mechanical effects on free radicals in UHMWPE joints during implantation", J. Biomed. Material Res., 25: 1005-1016 (1991).

"Standard Practice for Dosimetry in an Electron Bean Facility for Radiation Processing at Energies Between 300 keV and 25 keV", Am. Soc. for Testing & Materials, Designation: E1649-94, 870-888 (1995).

Oonishi, H. et al., "The Low Wear of Cross-Linked Polyethylene Socket in Total Hip Prostheses", Encyclopedic Handbook of Biomaterials & Bioengineering, vol. 2, Marcel Dekker, Inc., 1853-1868 (1995).

Atkinson, J. et al., "The nature of silane cross-linked HDPE is discussed. Creep and wear tests indicate its potential as a possible replacement for high molecular weight polyethylene in prostheses", Polymers in Medicine and Surgery, Conf. Held by Plastics and Rubber Institute and Biological Engineering Soc., UK. Sep, P4/1-P4/9 (1986).

Jones, W. et al., Effect of γIrradiation on the Friction and Wear of Ultrahigh Molecular Weight Polyethylene, Wear 70: 77-92 (1981).

Gent, A. et al., "Elastic Behavior, Birefringence, and Swelling of Amorphous Polyethylene Networks", J. Polymer Sci. 5: 47-60 (1967).

Zoepfl, F. et al., "Differential Scanning Calorimetry Studies of Irradiated Polyethylene: I. Melting Temperatures and Fusion Endotherms", J. Polymer Sci. Polym. Chem. Ed., 22: 2017-2032 (1984).

Zoepfl, F. et al., "Differential Scanning Calorimetry Studies of Irradiated Polyethylene: II. The Effect of Oxygen", J. Polymer Sci. Polym. Chem. Ed., 22: 2032-2045 (1984).

Mandelkem, L. et al., "Fusion of Polymer Networks Formed from Linear Polyethylene: Effect of Intermolecular Order", contribution from the General Electric Research Laboratory and from the Polymer Structure Section, National Bureau of Standards 82: 46-53 (1960).

Muratoglu, O.K. et al., "A Comparison of 5 Different Types of Highly Crosslinked UHMWPES: Physical Properties and Wear Behavior", 45$^{th}$ Annual Meeting, Orthopaedic Research Society, Anaheim, CA, Feb. 1-4, 77 (1999).

Muratoglu, O.K. et al., "A Novel Method of Crosslinking UHMWPE to Improve Wear With Little or No Sacrifice on Mechanical Properties", 45$^{th}$ Annual Meeting, Orthopaedic Research Society, Anaheim, CA, Feb. 1-4, 829 (1999).

Muratoglu, O.K. et al., "Electron Beam Cross Linking of UHMWPE At Room Remperature, A Candidate Bearing Material for Total Joint Arthroplasty", 23rd Annual Meeting of the Society for Biomaterials, New Orleans, Louisana, Apr. 30-May 4, 74 (1997).

Matsubara, K et al., "The Wear Properties of High-Density Polyethylene Irradiated by Gamma Rays", Wear 10: 214 (1967).

McKellop, H. et al., "Increased Wear of UHMW Polyethylene After Gamma Radiation Sterilization", Trans. 26$^{th}$ Ann. ORS, Atlanta, Georgia, Feb. 5-7 (1980).

McKellop, H., "The Effect of Radiation and Ethylene Oxide Sterilization on the Wear of UHMW Polyethylene", 7$^{th}$ European Conference on Biomaterials, Sep. 8-11, (1987).

Shen, F-S. et al., "Irradiation of Chemically Crosslinked Ultrahigh Molecular Weight Polyethylene", J. Polymer Sci.: Part B: Polymer Phys. 34: 1063-1077 (1996).

Oka, M. et al., "Wear-Resistant Properties of Newly Improved UHMWPE", Trans. Fifth World Biomaterials Congress, Toronto, Canada 520, (May 29-Jun. 2, 1996).

Bellare, A. et al., "Deformation, Morphology and Wear Behavior of Polyethylene", Trans. 23$^{rd}$ Ann. Mtg., Soc. Biomaterials, New Orleans, Louisiana, 75 (Apr. 30-May 4, 1997).

Clarke, I.C. et al., "Simulator Wear Study of High-Dose Gamma-Irradiated UHMWPE Cups", Trans. 23$^{rd}$ Ann. Mtg., Soc. Biomaterials, New Orleans, LA, 71, (Apr. 30-May 4, 1997).

Taylor, G. et al., "Stability of $N_2$ Packaged Gamma Irradiated UHMWPE", Trans. 23$^{rd}$ Ann. Mtg., Soc. Biomaterials, New Orleans, LA, 421, (Apr. 30-May 4, 1997).

Taylor, G. et al., "Stability of $N_2$ Packaged Gamma Irradiated UHMWPE", Trans. 43$^{rd}$ Ann. Mtg., Orthopaedic Res. Soc., San Francisco, California, 776 (Feb. 9-13, 1997).

McKellop, H. et al., "The Effect of Sterilization Method, Calcium Stearate and Molecular Weight on Wear of UHMWPE Acetabular Cups", Trans. 23$^{rd}$ Ann. Mtg., Soc. Biomaterials, New Orleans, LA, 43 (Apr. 30-May 4, 1997).

McKellop, H. et al., "Effect of Sterilization Method on the Wear Rate of UHMW Polyethylene Acetabular Cups in a Hip Simulator", Trans. 43$^{rd}$ Ann. Mtg., Orthopaedic Res. Soc. San Francisco, CA, 7, 94-16 Feb. 9-13 (1997).

McKellop, H. et al., "Wear of UHMWPE Acetabular Cups After Gamma Sterilization in Nitrogen, Thermal Stabilization and Artificial Aging", Trans. 23$^{rd}$ Ann. Mtg., Soc. Biomaterials, New Orleans, LA, Apr. 30-May 4, 45 (1997).

Wang, A. et al., "Effect of Radiation Dosage on the Wear of Stabilized UHMWPE Evaluated by Hip and Knee Joint Simulators", Trans. 23$^{rd}$ Ann. Mtg., Soc. Biomaterials, New Orleans, LA, 394 (Apr. 30-May 4, 1997).

Wang, A. et al., "Wear Mechanisms and Wear Testing of Ultra-High Molecular Weight Polyethylene in Total Joint Replacements", Hand-Out for Polyethylene Wear in Orthopaedic Implants Workshop, Trans. 23$^{rd}$ Ann. Mtg., Soc. Biomaterials, New Orleans, LA (Apr. 30-May 4, 1997).

Yu, Y.J. et al., "Oxidation of UHMWPE Acetabular Cups After Sterilization and Wear Testing in a Hip Joint Simulator", Trans. 43$^{rd}$ Ann. Mtg., Orthopaedic Res. Soc. San Francisco, CA, 778 (Feb. 9-13, 1997).

Roe, R. et al., "Effect of Radiation Sterilization and Aging on Ultrahigh Molecular Weight Polyethylene", Journal of Biomedical Materials Research, 15:209-230 (1981).

Li, S. et al., "Chemical Degradation of Polyethylene in Hip and Knee Replacements", 38$^{th}$ Ann. Mtg., Orthopaedic Research Society, Washington, D.C., 41, (Feb. 7-20, 1992).

Kurtz, S.M. et al.,. "Post-Irradiation Aging and the Stresses in UHMWPE Components for Total Joint Replacement", 40$^{th}$ Ann. Mtg., Orthopaedic Research Society, New Orleans, LA, 584, (Feb. 21-24 1994).

Lancaster et al., "Friction and Wear", in Jenkins (ed): Polymer Science, 959, 1045, North Holland Publishing Company (1972).

McKellop, H. et al., "Accelerated Aging of Irradiated UHMW Polyethylene for Wear Evaluations", 42$^{nd}$ Annual Meeting, Orthopaedic Research Society, Atlanta, Georgia, 483, (Feb. 19-22, 1996).

Blunn, G.W. et al., "The Effect of Oxidation on the Wear of Untreated and Stabilized UHMWPE", 42$^{nd}$ Annual Meeting, Orthopaedic Research Society, Atlanta, Georgia, 482, (Feb. 19-22, 1996).

"Duration™ Stabilized UHMWPE: an UHMWPE with Superior Wear and Oxidation Resistance; Technical Development and Scientific Evaluation", (Cover sheet and reference page).

Sun, D.C. et al.,"The Origin of the White Band Observed in Direct Compression Molded UHMWPE Inserts", 20$^{th}$ Annual Meeting Society for Biomaterials, 121 (Apr. 5-9, 1994).

Sun, D.C. et al., "On the Origins of a Subsurface Oxidation Maximum and its Relationship to the Performance of UHMWPE Implants", 21$^{st}$ Annual Meeting, Society for Biochemicals, San Francisco, CA, 362: (Mar. 18-22, 1995).

Premnath, V. et al., "Melt Irradiated UHMWPE for Total Hip Replacement: Synthesis & Properties", 43$^{rd}$ Annual Meeting, Orthopedic Res. Soc., San Francisco, CA, 91-16, (Feb. 9-13, 1997).

Muratoglu, O.K. et al., "The Effect of Temperature on Radiation Crosslinking of UHMWPE for Use in Total Hip Arthroplasty", 46$^{th}$ Annual Meeting, Orthopaedic Res. Soc., Orlando, FL, 0547 (Mar. 12-15, 2000).

D.C. Sun, C. Stark, J.H. Dumbleton, "Development of an Accelerated Aging Method For Evaluation of Long-term Irradiation Effects on UHMPWE Implants", Polymer Preprints, vol. 35, No. 2, pp. 969-970, (1994).

A.F. Booth, "Industrial Sterilization Technologies: New and Old Trends Shape Manufacturer Choices", Medical Device & Diagnostic Industry, pp. 64-72, Feb. (1995).

B. Hinsch, "Sterilization Methods for Implants Made of UHMWPE", in Ultra-High Molecular Weight Polyethylene as Biomaterials in Orthopedic Surgery, Toronto: Hogrefe & Huber Publishers, pp. 63-65, (1991).

"Irradiation Effects on Polymers", edited by D.W. Clegg and A.A. Collyer, Elsevier Applied Science, London, (1991).

"Radiation Effects on Polymers", edited by R. L. Clough and S. W. Shalaby, ACS Symposium Series 475, (1991).

P. Eyerer, M. Kurth, H. A. McKellop and T. Mittimeier, "Characterization of UHMWPE hip cups run on joint stimulators", J. Biomedical Materials Research, vol. 21, pp. 275-291, (1987).

A. Wang, D.C. Sun, C.Stark, J.H. Dumbleton, Wear, pp. 181-183:241-249 (1995).

A. Wang, C. Stark, J.H. Dumbleton, "Role of cyclic plastic deformation in the wear of UHMWPE acetabular cups", Journal of Biomedical Materials Research, vol. 29, pp. 619-626, (1995).

A. Edidin et al., "Enhancement of multiaxial mechanical behavior by slot drawing of UHMWPE: a candidate biomaterial for total knee arthroplasty," 46$^{th}$ Annual Mtg., Orthopaedic. Res. Soc., Mar. 12-15, Orlando, FL (2000).

Watkins et al."Fractionation of High Density Polyethylene in Propane by Isothermal Pressure Profiling and Isobaric Temperature Profiling" J. Supercritical Fluids, 4:24-31 (1994).

Q. Qiu, Ph. D. et al., "Formation and Differentiation of Three-Dimensional Rat Marrow Stromal Cell Culture on Microcarriers in a Rotating -Wall Vessel", Tissue Engineering, vol. 4, No. 1, 1998.

Qing-Qing Qiu et al., "Fabrication, characterization and evaluation of bioceramic hollow microspheres used as microcarriers for 3-D bone tissue formation in rotating bioreactors", Biomaterials 20, p. 989-1001, 1999.

Robert Langer, "New Methods of Drug Delivery", Science, 249, Articles, p. 1527-1533. Sep. 28, 1990.

Larry L. Hench, "Bioactive Ceramics", Annals New York Academy of Sciences, p. 54-71.

Paul Ducheyne, "Stimulation of Biological Function with Bioactive Glass", MRS Bulletin, p. 43-49, Nov. 1998.

Q. Qiu, et al., "A novel bioactive, resorbable composite microsphere for bone tissue engineering and regeneration", Society for Biomaterials, Sixth World Biomaterials Congress Transactions, p. 433, 2000.

Mutsuhiro Maeda, et al., "Histological Study of Carboxymethylchitn/Hydroxyapatite Composite for Bone Repair", Society for Biomaterials, 27$^{th}$ Annual Meeting Transactions, p. 416, 2001.

Fu-Wen Shen, PhD et al., "Surface-Gradient Cross-linked Polyethylene Acetabular Cups—Oxidation Resistance and Wear against Smooth and Rough Femoral Balls", Clinical Orthopaedics and Related Research, No. 430, 2005, pp. 80-88.

Harry McKellop et al., "Development of an Extremely Wear-Resistant Ultra High Molecular Weight Pothylene for Total Hip Replacements", Journal of Orthopaedic Research, vol. 17, No. 2, 1999, pp. 157-167.

L. Martinotto et al., "Space Charge Behavior of Chemically Cross-linked and Radiation Cross-linked Polyethylene", 2000 Conference on Electrical Insulation and Dielectric Phenomena—IEEE, pp. 109-112.

* cited by examiner

ORTHOPAEDIC BEARING AND METHOD FOR MAKING THE SAME

CROSS REFERENCE

Cross reference is made to copending U.S. patent application Ser. No. 11/027,100 entitled "Orthopaedic Bearing and Method of Making the Same" and Ser. No. 11/027,099 entitled "Orthopaedic Bearing and Method of Making the Same", both of which are assigned to the same assignee as the present application, are filed concurrently herewith, and are hereby incorporated by reference.

FIELD OF THE DISCLOSURE

The present disclosure relates generally to implantable orthopaedic bearings and methods of making the same.

BACKGROUND

Implantable orthopaedic bearings, such as glenoid bearings, are typically made with polyethylene. One type of polyethylene commonly used in the fabrication of such bearings is Ultra-High Molecular Weight Polyethylene (UHMWPE). Certain characteristics of UHMWPE may be enhanced by exposing it to radiation such as gamma radiation. In particular, exposing UHMWPE to predetermined doses of radiation crosslinks the UHMWPE thereby increasing its wear resistance. Techniques for crosslinking, quenching, or otherwise preparing UHMWPE are described in numerous issued U.S. patents, examples of which include U.S. Pat. No. 5,728,748 (and its counterparts) issued to Sun, et al, U.S. Pat. No. 5,879,400 issued to Merrill et al, U.S. Pat. No. 6,017,975 issued to Saum, et al, U.S. Pat. No. 6,242,507 issued to Saum et al, U.S. Pat. No. 6,316,158 issued to Saum et al, U.S. Pat. No. 6,228,900 issued to Shen et al, U.S. Pat. No. 6,245,276 issued to McNulty et al, and U.S. Pat. No. 6,281,264 issued to Salovey et al. The disclosure of each of these U.S. patents is hereby incorporated by reference.

SUMMARY

According to one aspect of the disclosure, an orthopaedic bearing includes a metallic component having a polymer composite secured thereto. The polymer composite may include a non-crosslinked layer of polymer and a crosslinked layer of polymer. The non-crosslinked layer of polymer may be positioned between the metallic component and a crosslinked layer of polymer.

The crosslinked layer of polymer may have an articulating surface defined therein.

The crosslinked layer of polymer may include gamma irradiated polymer.

Both layers of polymer may include polyethylene. The polyethylene may be UHMWPE.

The metallic component may include a solid metal body with a porous coating disposed thereon.

The metallic component may include a porous metal body.

In lieu of a non-crosslinked layer of polymer, a layer of polymer which has been crosslinked to a lesser degree than the crosslinked layer may be used.

According to another aspect of the disclosure, a method of making an orthopaedic bearing includes securing a polymer composite to a metallic component. The polymer composite may be molded to the metallic component. The polymer composite may be compression molded to the metallic component.

The polymer composite may include a non-crosslinked layer of polymer and a crosslinked layer of polymer. The non-crosslinked layer of polymer may be positioned between the metallic component and a crosslinked layer of polymer.

An articulating surface may be molded into the crosslinked layer of polymer.

The crosslinked layer of polymer may include gamma irradiated polymer.

Both layers of polymer may include polyethylene. The polyethylene may be UHMWPE.

Both layers of polymer and the metallic component may be molded in a single molding process. The layers of polymer may first be molded to one another, and thereafter molded to the metallic component in a subsequent molding process. The non-crosslinked layer of polymer may first be molded to the metallic component, with the crosslinked layer of polymer being molded to the non-crosslinked layer of polymer in a subsequent molding process.

A polymer preform may be used as the starting material for one or both of the crosslinked layer of polymer and the non-crosslinked layer of polymer.

A polymer powder may be used as the starting material for one or both of the crosslinked layer of polymer and the non-crosslinked layer of polymer.

The metallic component may include a solid metal body with a porous coating disposed thereon.

The metallic component may include a porous metal body.

In lieu of a non-crosslinked layer of polymer, a layer of polymer which has been crosslinked to a lesser degree than the crosslinked layer may be used.

The above and other features of the present disclosure will become apparent from the following description and the attached drawings.

BRIEF DESCRIPTION OF THE DRAWINGS

The detailed description particularly refers to the accompanying figures in which.

DETAILED DESCRIPTION OF THE DRAWINGS

The present disclosure relates to implantable orthopaedic bearings and methods of making the same. Such bearings may be utilized in a number of joint replacement or repair procedures such as surgical procedures associated with the shoulders, hips, knees, ankles, knuckles, or any other joint. As such, although the following description illustrates one exemplary type of bearing (i.e., a glenoid bearing), it should be appreciated that the invention is not limited to glenoid bearings and may find applicability in the design of any type of orthopaedic bearing.

Figure 1:
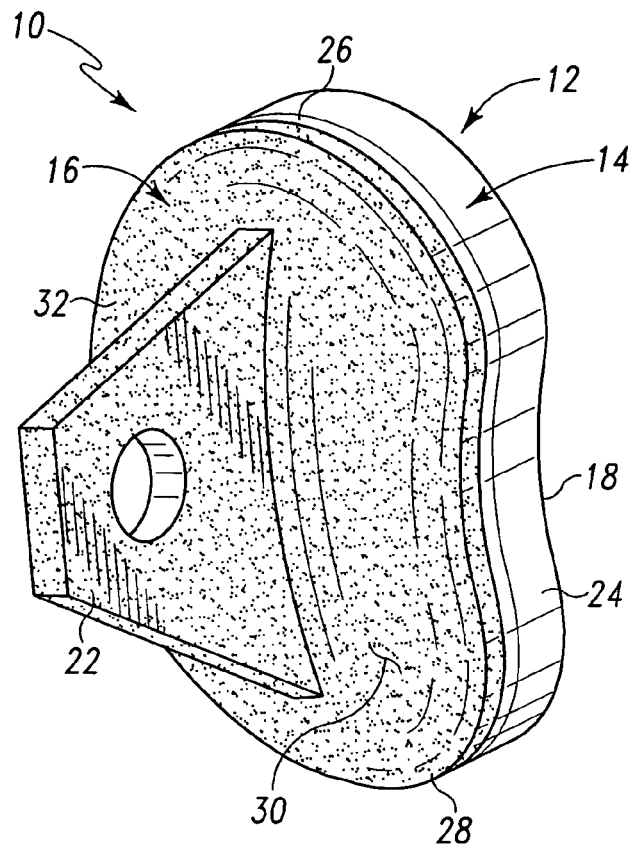
FIG. 1 is a perspective view of an implantable glenoid bearing.
Figure 2:
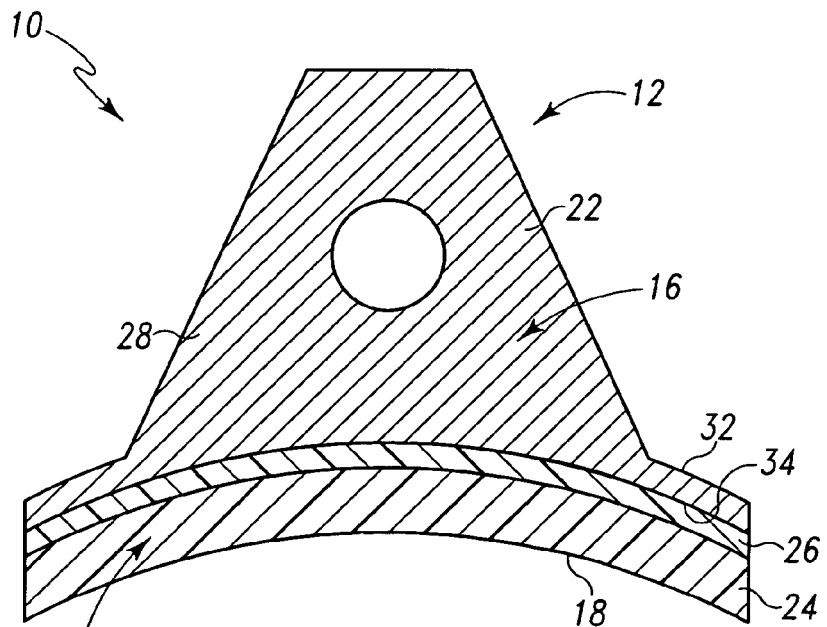
FIG. 2 is a cross sectional view of the glenoid bearing of FIG. 1.
Figure 3:
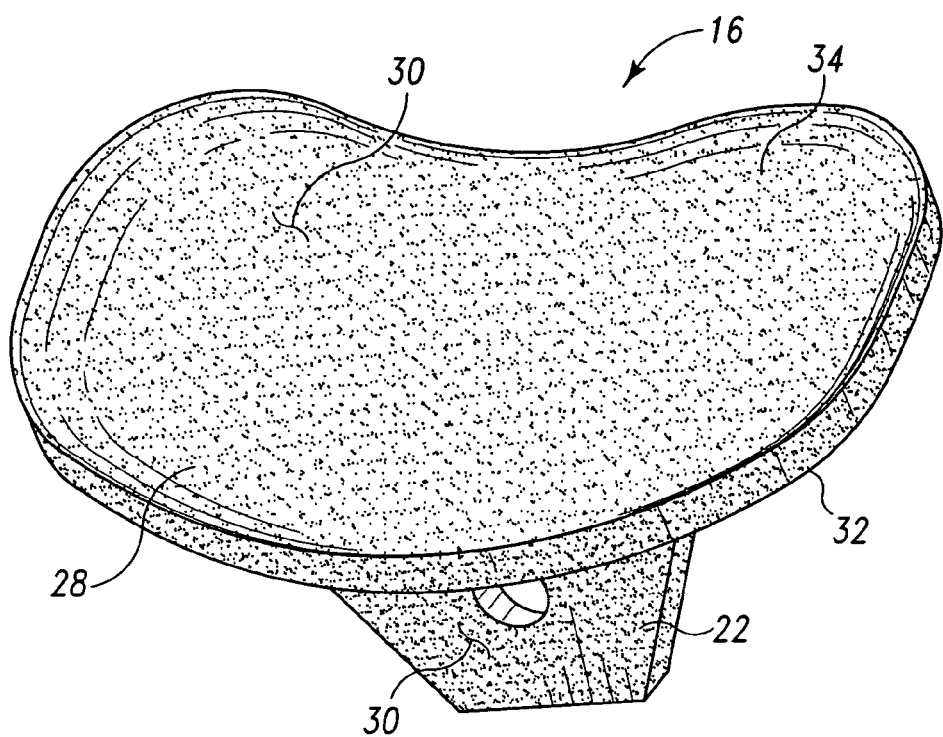
FIG. 3 is a perspective view of the metallic component of the glenoid bearing of FIG. 1.

Referring now to FIGS. 1-3, there is shown an implantable orthopaedic bearing 10 such as a one-piece glenoid bearing 12 for implantation into a glenoid of a patient (not shown). The glenoid bearing 12 has a polymer composite 14 secured to a metallic component 16. The polymer composite 14 has an articulating or bearing surface 18 on which a natural or prosthetic component bears. For example, a natural or prosthetic humeral head (not shown) bears on the articulating surface 18 when the glenoid bearing 12 is implanted into a patient. The metallic component 16 has a keel 22 defined therein. The keel 22 is inserted into a surgically formed slot (not shown) in the glenoid surface of the patient. The keel 22 may be press fit or held in place by the use of bone cement. It should be appreciated that the metallic component 16 may be embodied with attachment features other than the keel 22. For example, the metallic component 16 may be embodied with one or more pegs.

The polymer composite 14 has a number of polymer layers 24, 26. The polymer layer 24 of the composite 14 is constructed with a material which possesses mechanical properties favorable for use in the construction of the articulating surface 18 (e.g., enhanced wear and oxidation resistance). The polymer layer 26, on the other hand, is constructed of a material which possesses mechanical properties favorable for use in securing the polymer layer 24 to the metallic component 16. It should be appreciated that, as used herein, the term "layer" is not intended to be limited to a "thickness" of material positioned proximate to another similarly dimensioned "thickness" of material, but rather is intended to include numerous structures, configurations, and constructions of material. For example, the term "layer" may include a portion, region, or other structure of material which is positioned proximate to another portion, region, or structure of differing material.

As used herein, the term "polymer" is intended to mean any medical grade polymeric material which may be implanted into a patient. A specific example of such a polymer is medical grade polyethylene. The term "polyethylene", as defined herein, includes polyethylene, such as a polyethylene homopolymer, high density polyethylene, high molecular weight polyethylene, high density high molecular weight polyethylene, ultrahigh molecular weight polyethylene, or any other type of polyethylene utilized in the construction of a prosthetic implant. A more specific example of such a polymer is medical grade UHMWPE. The term "polymer" is also intended to include both homopolymers and copolymers. The term "polymer" also includes oriented materials, such as the materials disclosed in copending U.S. patent application Ser. No. 09/961,842 entitled "Oriented, Cross-Linked UHMWPE Molding for Orthopaedic Applications", which was filed on Sep. 24, 2001 by King et al., which is hereby incorporated by reference, and which is owned by the same assignee as the present application.

The term "polymer" is also intended to include high temperature engineering polymers. Such polymers include members of the polyaryletherketone family and the polyimide family. Specific members of the polyaryletherketone family include polyetherketoneetherketoneketone, polyetheretherketone, and polyetherketone.

In one exemplary embodiment, a polymer composite 14 is utilized in which the polymer layer 24 is made with a crosslinked polymer, whereas the polymer layer 26 is made with a non-crosslinked polymer. In a more specific exemplary embodiment, the polymer utilized in the construction of both polymer layers 24, 26 of the polymer composite 14 is polyethylene. One particularly useful polyethylene for use in the construction of the polymer layers 24, 26 is UHMWPE.

As described above, a polymer may be crosslinked by, for example, exposure to radiation such as gamma radiation. As such, the polymer layer 24 (i.e., the crosslinked polymer layer) of the polymer composite 14 of this exemplary embodiment may be fabricated by exposing the polymer layer 24 to gamma radiation. Such exposure may be in the exemplary range of 10-150 KGy. The polymer layer 26 (i.e., the non-crosslinked polymer layer) of the polymer composite 14 of this exemplary embodiment is not exposed to such gamma radiation. In a more specific exemplary embodiment, the polymer layer 24 (and hence the articulating surface 18 formed therein) is constructed of a crosslinked polyethylene such as crosslinked UHMWPE, whereas the polymer layer 26 is constructed of a non-crosslinked polyethylene such as a non-crosslinked UHMWPE.

In another exemplary embodiment, a polymer composite 14 is utilized in which the polymer layer 24 is made from a polymer which has been crosslinked to a first degree, whereas the polymer layer 26 is constructed from a polymer which has been crosslinked to a second degree. Specifically, the polymer layer 26 is made with a polymer which has been crosslinked to a lesser degree than the polymer utilized to make the polymer layer 24. One way to vary the degree in which a polymer is crosslinked is to vary the dose of radiation to which it is exposed. In a general sense, the greater the dose of radiation to which the polymer is exposed, the greater the degree in which the polymer is crosslinked. As such, in regard to the polymer composite 14 of this exemplary embodiment, the polymer layer 24 is exposed to a first dose of gamma radiation, whereas the polymer layer 26 is exposed to a second, different dose of gamma radiation. In a more specific exemplary embodiment, the dose of gamma radiation to which the polymer layer 26 is exposed is less than the dose of radiation to which the polymer layer 24 is exposed.

Hence, in a specific implementation of the polymer composite 14 of this exemplary embodiment, the first polymer layer 24 may be made from a polyethylene such as UHMWPE which has been exposed to a first dose of gamma radiation. The second layer 26, on the other hand, may be made with a polyethylene such as UHMWPE which has been exposed to a second, different dose of gamma radiation. It should be appreciated that the dose of gamma radiation to which the polyethylene of the polymer layer 26 is exposed is less than the dose of radiation to which the polyethylene of the polymer layer 24 is exposed. It should be appreciated that the polymer layer 26 of this exemplary polymer composite 14, although crosslinked to some degree, still possesses many favorable mechanical characteristics to facilitate securing the more highly crosslinked polymer layer 24 to the metallic component 16.

As alluded to above, the material from which the polymer layer 26 is made may include polymers other than polyethylene. For example, the polymer layer 26 may be made with poly methyl methacrylate (PMMA). Along a similar line, although crosslinked polymers are believed at present to provide superior wear resistance and oxidation resistance for the articulating surface in orthopaedic implants, new materials may be developed in the future with improved properties. Accordingly, the present invention is not limited to any particular material, and may encompass newly developed materials, unless a particular material is expressly set forth in the claims.

Referring in particular now to FIG. 3, the metallic component 16 has a metal body 28 which is made from an implantable metal such as stainless steel, cobalt chrome, titanium, or the like. The metal body has a porous coating 30 disposed thereon. The porous coating 30 facilitates bony ingrowth to the backside 32 and keel 22 of the metallic component 16. Moreover, in the case of when bone cement is used, the porous coating 30 enhances fixation to the backside 32 and keel 22 of the metallic component 16. The porous coating 30 is also disposed on the surface 34 on which the polymer composite 14 is molded. During the molding process, the polymer layer 26 is forced into or otherwise interdigitates with the porous coating 30 thereby enhancing the mechanical connection therebetween. One type of porous coating which may be used as the porous coating 30 is Porocoat® Porous Coating which is commercially available from DePuy Orthopaedics of Warsaw, Ind.

The components of the one-piece glenoid component 12 (i.e., the metallic component 16, the polymer layer 24, and the polymer layer 26) may be assembled by use of a number of different techniques. One exemplary manner for doing so is by use of compression molding techniques. For example, the metallic component 16, the material from which the polymer layer 24 is to be made, and the material from which the polymer layer 26 is to be made may be placed in a mold with one another. Thereafter, the components are compression molded to one another under process parameters which cause the material from which the polymer layer 26 is made to be molten and fused to the material from which the polymer layer 24 is made thereby creating the polymer composite 14. At the same time, the material from which the polymer layer 26 is made is mechanically secured to the metallic component 16 by the compression molding process. As described above, the molten polymer layer 26 interdigitates with the porous coating 30 of the metallic component 16 when molded thereto. It should also be appreciated that the mold may be configured to not only fuse the components to one another, but also form the articulating surface 18 into the polymer composite 14.

Other methods of compression molding the one-piece glenoid bearing 12 are also contemplated. For example, in lieu of contemporaneously molding the components of the one-piece glenoid component 12 (i.e., the metallic component 16, the polymer layer 24, and the polymer layer 26) to one another in a single molding process, multiple molding processes may be employed. For instance, the polymer composite 14 may be formed in a first molding process by compression molding the material from which the polymer layer 24 is to be made and the material from which the polymer layer 26 is to be made to one another. Thereafter, the polymer composite 14 and the metallic component 16 may be molded to one another in a separate mold process.

In another multi-step molding process, the material from which the polymer layer 26 is to be made may be molded to the metallic component 16 in a first molding process. Thereafter, in a second molding process, the material from which the polymer layer 24 is to be made is molded onto the polymer layer 26.

The starting composite materials (e.g., polymers such as polyethylene) for use in the molding process may be provided in a number of different forms. For example, each of the starting materials may be provided as a preform. What is meant herein by the term "preform" is an article that has been consolidated, such as by ram extrusion or compression molding of polymer resin particles, into rods, sheets, blocks, slabs, or the like. The term "preform" also includes a preform "puck" which may be prepared by intermediate machining of a commercially available preform. Polymer preforms such as polyethylene preforms may be provided in a number of different pre-treated or preconditioned variations. For example, crosslinked or non-crosslinked (e.g., irradiated or non-irradiated) preforms may be utilized. Such preforms may be treated to eliminate (e.g., re-melting or quenching) or stabilize (e.g., the addition of vitamin E as an antioxidant) any free radicals present therein. Alternatively, the preforms may not be treated in such a manner.

The starting composite materials (e.g., polymers and copolymers) may also be provided as powders. What is meant herein by the term "powder" is resin particles. Similarly to as described above in regard to preforms, powders may be provided in a number of different pre-treated or preconditioned variations. For example, crosslinked or non-crosslinked (e.g., irradiated or non-irradiated) powders may be utilized.

It should be appreciated that the starting composite materials (e.g., the preforms or powders) may be "pre-irradiated", "pre-treated to eliminate or stabilize free radicals", or otherwise preconditioned prior to use thereof. In particular, it may be desirable for a manufacturer of prosthetic bearings to purchase material (e.g. polyethylene) which has been irradiated (or otherwise crosslinked), pre-treated to eliminate or stabilize free radicals, or otherwise preconditioned by a commercial supplier or other manufacturer of the material. Such "out-sourcing" of preconditioning processes is contemplated for use in the processes described herein.

In regard to fabrication of a bearing 12 having a polymer composite 14 in which the polymer layer 24 is made of crosslinked polymer and the other polymer layer 26 is made of non-crosslinked polymer, a preform of polymer which is non-crosslinked (i.e., non-irradiated) may be positioned in a mold between a preform of crosslinked polymer (i.e., pre-irradiated) and the metallic component 16. Thereafter, the metallic components and the two preforms are compression molded under process parameters which cause the non-crosslinked preform of polymer to be (i) molten and fused to the preform of crosslinked polymer, and (ii) molten and mechanically secured to the metallic component 16. It should also be appreciated that during such a molding process, the articulating surface 18 is formed in the resultant polymer composite 14. Moreover, during such a molding process, the polymer associated with the layer 26 is interdigitated with the porous coating 30 of the metallic component 16. In an exemplary implementation of this process, a preform of a crosslinked polyethylene such as crosslinked UHMWPE is compression molded to a preform of a non-crosslinked polyethylene such as non-crosslinked UHMWPE, which is, in turn, molded to the metallic component 16. As alluded to above, such a fabrication process may be performed in a number of different molding steps. For example, the two preforms may first be molded to one another, with the resultant polymer composite then being molded to the metallic component 16 in a subsequent molding process. Alternatively, the non-crosslinked polymer preform may first be molded to the metallic component 16, with the crosslinked polymer preform being molded to the non-crosslinked layer in a subsequent molding process.

Such a polymer composite 14 (i.e., the polymer layer 24 made of crosslinked polymer and the polymer layer 26 made of non-crosslinked polymer) may also be fabricated by the use of polymer powders. For example, polymer powder which is non-crosslinked (i.e., non-irradiated) may be placed in a mold between a preform of crosslinked polymer (i.e., pre-irradiated) and the metallic component 16. Thereafter, the components are compression molded under process parameters which cause the non-crosslinked polymer powder to be (i) molten and fused to the preform of crosslinked polymer, and (ii) molten and mechanically secured to the metallic component 16. It should also be appreciated that during such a molding process, the articulating surface 18 is formed in the resultant polymer composite 14. Moreover, during such a molding process, the polymer associated with the layer 26 is interdigitated with the porous coating 30 of the metallic component 16. In an exemplary implementation of this process, the crosslinked preform may be provided as a crosslinked polyethylene preform such as a crosslinked UHMWPE preform, whereas the non-crosslinked powder may be provided as a non-crosslinked polyethylene powder such as a non-crosslinked UHMWPE powder. Similarly to as described above in regard to use of two preforms, the fabrication process may be performed in a number of different molding steps. For example, the crosslinked preform and the non-crosslinked powder may first be molded to one another, with the resultant polymer composite then being molded to the metallic component 16 in a subsequent molding process. Alternatively, the non-crosslinked polymer powder may first be molded to the metallic component 16, with the crosslinked polymer preform being molded to the non-crosslinked layer in a subsequent molding process.

In regard to fabrication of a bearing 12 having of a polymer composite 14 in which the polymer layer 24 is made of a polymer which has been crosslinked to a first degree and the other polymer layer 26 is made of a polymer which has been crosslinked to a second, lesser degree, a preform of polymer which is crosslinked to the second (lesser) degree may be positioned in a mold between a preform of the polymer which has been crosslinked to the first (greater) degree and the metallic component 16. Thereafter, the metallic components and the two preforms are compression molded under process parameters which cause the lesser crosslinked preform of polymer to be (i) molten and fused to the preform of greater crosslinked polymer, and (ii) molten and mechanically secured to the metallic component 16. It should also be appreciated that during such a molding process, the articulating surface 18 is formed in the resultant polymer composite 14. Moreover, during such a molding process, the polymer associated with the layer 26 is interdigitated with the porous coating 30 of the metallic component 16. In an exemplary implementation of this process, a preform of polyethylene such as UHMWPE which is crosslinked to a first degree is compression molded to a preform of polyethylene such as UHMWPE which is crosslinked to a second, lesser degree, which is, in turn, molded to the metallic component 16. In a similar manner to as described above, this fabrication process may also be performed in a number of different molding steps. For example, the two preforms may first be molded to one another, with the resultant polymer composite then being molded to the metallic component 16 in a subsequent molding process. Alternatively, the lesser crosslinked polymer preform may first be molded to the metallic component 16, with the greater crosslinked polymer preform being molded to the lesser crosslinked layer in a subsequent molding process.

Such a polymer composite 14 (i.e., a polymer layer 24 constructed of a polymer which has been crosslinked to a first degree and a polymer layer 26 constructed of a polymer which has been crosslinked to a second, lesser degree) may also be fabricated by the use of polymer powders. For example, polymer powder which is crosslinked to the second (lesser) degree may be placed in a mold between a preform of polymer crosslinked to the first (greater) degree and the metallic component 16. Thereafter, the components are compression molded under process parameters which cause the lesser crosslinked polymer powder to be (i) molten and fused to the preform of greater crosslinked polymer, and (ii) molten and mechanically secured to the metallic component 16. It should also be appreciated that during such a molding process, the articulating surface 18 is formed in the resultant polymer composite 14. Moreover, during such a molding process, the polymer associated with the layer 26 is interdigitated with the porous coating 30 of the metallic component 16. In an exemplary implementation of this process, a powder of polyethylene such as UHMWPE which is crosslinked to a first degree is compression molded to a preform of polyethylene such as UHMWPE which is crosslinked to a second, lesser degree. Similarly to as described above in regard to use of two preforms, the fabrication process may be performed in a number of different molding steps. For example, the greater crosslinked preform and the lesser crosslinked powder may first be molded to one another, with the resultant polymer composite then being molded to the metallic component 16 in a subsequent molding process. Alternatively, the lesser crosslinked polymer powder may first be molded to the metallic component 16, with the greater crosslinked polymer preform being molded to the lesser crosslinked layer in a subsequent molding process.

It should also be appreciated that although the composites 14 have herein been described as having two layers, other composite configurations are also contemplated. For example, the polymer composite 14 may be configured to include several alternating layers of materials similar to the materials used in regard to the two-layer composites described above. For instance, the polymer composite 14 may be configured to include several (i.e., more than two) layers of alternating crosslinked and non-crosslinked UHMWPE. It should also be appreciated that more than two different material types may also be used in the construction of the composite. For example, a third material type may be used as an adhesion promoter between two layers (or between a layer and the underlying (e.g., metallic) component).

Moreover, it may be desirable to use vacuum molding for some materials. For example, vacuum molding may be preferred where one or more of the layers include a non-quenched material.

Other methods of securing the two polymer layers can be used for some applications. For example, instead of melt-fusion, mechanical interlocks can be used in some applications. With the choice of appropriate materials and processes, mechanical interlocks between polymer layers may provide an interface with adequate mechanical and dynamic properties. For an application relying upon mechanical interlocks, it is believed that mechanical interlocking with adequate interfacial strength can be achieved by providing a layer of polymer 26 having a porous structure of a high-temperature engineering polymer, such as one from the polyaryletherketone family or the polyimide family, and by control of process parameters. In such an application, a crosslinked UHMWPE layer may be used for the polymer layer 24 for the articulating surface. The crosslinked UHMWPE layer 24, in the form of a powder or preform, may be compression molded to the layer 26 of porous high temperature engineering polymer under a temperature that will melt at least a portion of the UHMWPE layer, so that UHMWPE melts into and fills some of the pores of the high temperature engineering material; when this UHMWPE material solidifies, the two polymer layers will be mechanically bonded together. The compression molding can be done at a temperature high enough to melt the UHMWPE layer but below the melting point of the polymer layer of polymer 26. The high temperature may be localized at the interface of the layers 24, 26. The porous structure may have a solid section.

The polymer layer 26 of porous high temperature engineering polymer may comprise an engineering polymer such as polyetheretherketone, polyetherketone, polyetherketoneetherketoneketone or polyimide. These materials are biocompatible and are able to withstand the processing temperature for UHMWPE without significant deformation. Preforms can be readily fabricated from these raw materials using conventional processing techniques. Although it is expected that these polymer materials will be useful as one of the polymer layers when relying upon a mechanical interlock, the present invention is not limited to these materials unless the claims expressly call for them. The present invention may also encompass newly developed polymers, unless a particular polymer is expressly set forth in the claims.

In addition, although the mechanical interlock that secures the two polymer layers together can be formed by compression molding the two polymer layers together, methods such as hot isostatic pressing may be used to secure the two layers of polymer 24, 26 together with a mechanical interlock. In addition, as new polymer materials are developed, new methods of securing the polymer layers together may also be developed. Accordingly, the present invention is not limited to any particular method of securing the polymer layers together, and may encompass newly developed materials and securing means, unless a particular material or process is expressly set forth in the claims.

Figure 4:
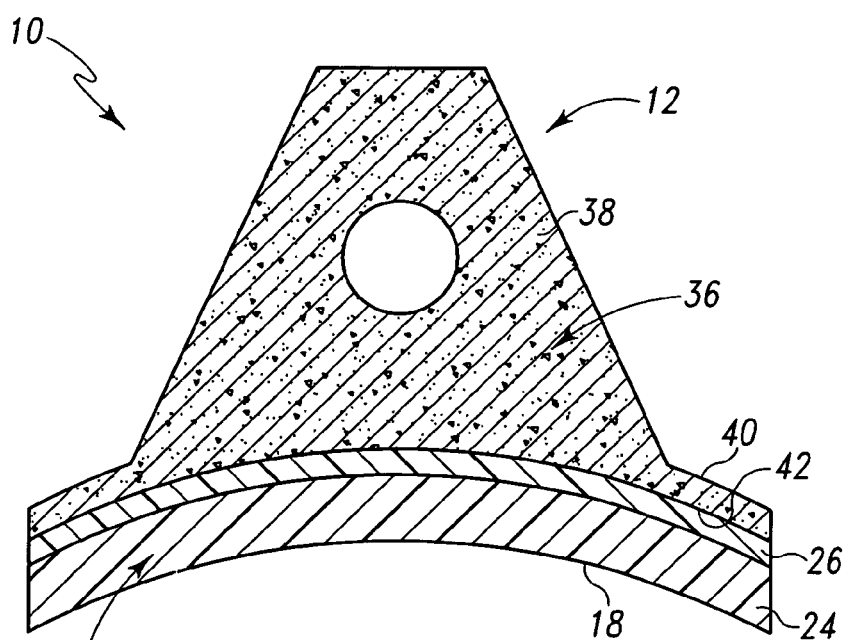
FIG. 4 is a cross sectional view similar to FIG. 2, but showing another embodiment of an implantable glenoid bearing.

Referring now to FIG. 4, there is shown another exemplary embodiment of the one-piece glenoid bearing 12. The glenoid bearing 12 of FIG. 4 is essentially the same as the bearing 12 of FIGS. 1 and 2 except for the configuration of the metallic component (which is designated with reference numeral 36 in FIG. 4). Specifically, in lieu of a solid metal body with a porous coating disposed thereon, the metallic component 36 of the glenoid bearing 12 of FIG. 4 has a porous metal body 38. As such, when the polymer of the polymer layer 26 is molded to the metallic component 36, the polymer is interdigitated with the porous metal body 38.

Prior to molding the polymer layer 26 to the porous metallic component 36, a sacrificial layer of polymer (not shown) may be molded to the backside 40 of the metallic component 36. The molding process may be controlled to allow the sacrificial layer of polymer to penetrate a predetermined distance into the metallic component 36. As such, when the polymer of the polymer layer 26 is molded to the front side 42 of the metallic component 36 the polymer of the polymer layer 26 is prevented from penetrating the entire thickness of the metallic component 36 by the sacrificial layer of polymer.

Once the polymer layer 26 has been molded to the metallic component 36 (with or without the polymer layer 24), the glenoid bearing 12 (or partially fabricated bearing 12) the sacrificial layer of polymer is removed by water extraction. This removes the sacrificial layer of polymer without disturbing the polymer layer 26 (and the polymer layer 24 if present) thereby exposing the porous backside 40 of the metallic component 36 (including the depth into its porous body 38 previously occupied by the sacrificial layer of polymer). Such exposed portions of the porous body promote bony ingrowth or cement adhesion into the glenoid bearing 12 when its implanted in a manner similar to as described above in regard to the porous coating 30 of the bearing 12 of FIGS. 1-3.

It should be appreciated that any desirable type of material may be used as the sacrificial layer of polymer. One type of such material is a meltable, high molecular weight hydrophilic polymer. A specific example of one such polymer is polyethylene oxide.

While the disclosure is susceptible to various modifications and alternative forms, specific exemplary embodiments thereof have been shown by way of example in the drawings and has herein be described in detail. It should be understood, however, that there is no intent to limit the disclosure to the particular forms disclosed, but on the contrary, the intention is to cover all modifications, equivalents, and alternatives falling within the spirit and scope of the disclosure.

There are a plurality of advantages of the present disclosure arising from the various features of the apparatus and methods described herein. It will be noted that alternative embodiments of the apparatus and methods of the present disclosure may not include all of the features described yet still benefit from at least some of the advantages of such features. Those of ordinary skill in the art may readily devise their own implementations of an apparatus and method that incorporate one or more of the features of the present disclosure and fall within the spirit and scope of the present disclosure.

For example, although it has been described herein to crosslink materials via irradiation, it should be appreciated that such materials may be crosslinked by any suitable technique. In addition, although the crosslinked polymer or more highly crosslinked polymer is typically be used for the articulating surface of the composite with non-crosslinked or less crosslinked polymer being used to facilitate securing the crosslinked polymer or more highly crosslinked polymer to the metallic component, there may be instances where it is desirable for the crosslinked polymer or more highly crosslinked polymer layer to be used to secure the non-crosslinked or less crosslinked polymer to the metallic bearing, with the latter layer being used for the articulating surface.

Moreover, in lieu of the of a metallic component, a ceramic component may be used in the fabrication of the orthopaedic bearing 10. In such a case, a porous ceramic component or porous coated ceramic component is used in lieu of the metallic component 16, with the bearing 10 being fabricated otherwise as described herein.

The invention claimed is:

1. A method of making an implantable orthopaedic bearing, the method comprising the steps of:
   molding a layer of non-crosslinked polyethylene to a ceramic component, and
   molding a layer of crosslinked polyethylene to the layer of non-crosslinked polyethylene such that a first side of the layer of crosslinked polyethylene is melt-fused to the layer of non-crosslinked polyethylene along a melt-fused interface that is devoid of mechanical interdigitation or interlocking, and
   forming an articulating surface on a second, opposite side of the layer of crosslinked polyethylene during the step of molding the layer of crosslinked polyethylene to the layer of non-crosslinked polyethylene.

2. The method of claim 1, wherein both molding steps are performed contemporaneously.

3. The method of claim 1, wherein the step of molding the layer of non-crosslinked polyethylene to the ceramic component is performed prior to the step of molding the layer of crosslinked polyethylene to the layer of non-crosslinked polyethylene.

4. The method of claim 1, wherein the step of molding the layer of non-crosslinked polyethylene to the ceramic component is performed after the step of molding the layer of crosslinked polyethylene to the layer of non-crosslinked polyethylene.

5. The method of claim 1, wherein:
   the step of molding the layer of crosslinked polyethylene to the layer of non-crosslinked polyethylene comprises molding the layer of crosslinked polyethylene to the layer of non-crosslinked polyethylene to form a polyethylene composite, and
   the step of molding the layer of non-crosslinked polyethylene to the ceramic component comprises molding the polyethylene composite to the ceramic component.

6. A method of making an implantable orthopaedic bearing, the method comprising the steps of:
   molding a first layer of polyethylene to a ceramic component, and
   molding a second layer of polyethylene to the first layer of polyethylene such that a first side of the second layer of polyethylene is melt-fused to the first layer of polyethylene along a melt-fused interface that is devoid of mechanical interdigitation or interlocking, the second layer of polyethylene being crosslinked to a greater degree than the first layer, and forming an articulating surface on a second, opposite side of the second layer of polyethylene during the step of molding the second layer of polyethylene to the first layer of polyethylene.

7. The method of claim 6, wherein both molding steps are performed contemporaneously.

8. The method of claim 6, wherein the step of molding the first layer of polyethylene to the ceramic component is performed prior to the step of molding the second layer of polyethylene to the first layer of polyethylene.

9. The method of claim 6, wherein the step of molding the first layer of polyethylene to the ceramic component is performed after the step of molding the second layer of polyethylene to the first layer of polyethylene.

10. The method of claim 6, wherein the step of molding the second layer of polyethylene to the first layer of polyethylene comprises compression molding the second layer of polyethylene and the first layer of polyethylene to one another.

11. The method of claim 6, wherein the step of molding the first layer of polyethylene to the ceramic component comprises compression molding the first layer of polyethylene to the ceramic component.

12. The method of claim 1, wherein molding the layer of crosslinked polyethylene to the layer of non-crosslinked polyethylene comprises molding a crosslinked polyethylene preform to a non-crosslinked polyethylene preform.

13. The method of claim 1, wherein molding the layer of crosslinked polyethylene to the layer of non-crosslinked polyethylene comprises molding a crosslinked polyethylene powder to a non-crosslinked polyethylene preform.

14. The method of claim 1, wherein molding the layer of crosslinked polyethylene to the layer of non-crosslinked polyethylene comprises molding a crosslinked polyethylene powder to a non-crosslinked polyethylene powder.

15. The method of claim 1, wherein molding the layer of crosslinked polyethylene to the layer of non-crosslinked polyethylene comprises molding a crosslinked polyethylene preform to a non-crosslinked polyethylene powder.

16. The method of claim 1, wherein molding the layer of non-crosslinked polyethylene to the ceramic component comprises molding a non-crosslinked polyethylene preform to the ceramic component.

17. The method of claim 1, wherein molding the layer of non-crosslinked polyethylene to the ceramic component comprises molding a non-crosslinked polyethylene powder to the ceramic component.

18. The method of claim 6, wherein:

molding the second layer of polyethylene to the first layer of polyethylene comprises molding a first polyethylene preform and a second polyethylene preform to one another, and the second polyethylene preform is crosslinked to a greater degree than the first polyethylene preform.

19. The method of claim 6, wherein:

molding the second layer of polyethylene to the first layer of polyethylene comprises molding a polyethylene preform and a polyethylene powder to one another, and the polyethylene powder is crosslinked to a greater degree than the polyethylene preform.

20. The method of claim 6, wherein:

molding the second layer of polyethylene to the first layer of polyethylene comprises molding a first polyethylene powder and a second polyethylene powder to one another, and the second polyethylene powder is crosslinked to a greater degree than the first polyethylene powder.

21. The method of claim 6, wherein:

molding the second layer of polyethylene to the first layer of polyethylene comprises molding a polyethylene preform and a polyethylene powder to one another, and the polyethylene powder is crosslinked to a lesser degree than the polyethylene preform.

22. The method of claim 6, wherein molding the first layer of polyethylene to the ceramic component comprises securing a polyethylene preform to the ceramic component.

23. The method of claim 6, wherein molding the first layer of polyethylene to the ceramic component comprises molding a polyethylene powder to the ceramic component.

* * * * *

UNITED STATES PATENT AND TRADEMARK OFFICE
CERTIFICATE OF CORRECTION

| | | |
|---|---|---|
| PATENT NO. | : 7,879,275 B2 | Page 1 of 1 |
| APPLICATION NO. | : 11/027662 | |
| DATED | : February 1, 2011 | |
| INVENTOR(S) | : Smith et al. | |

It is certified that error appears in the above-identified patent and that said Letters Patent is hereby corrected as shown below:

On the Title Page, Item (54) and col. 1 lines 1-2, replace the title with: --METHOD OF MAKING AN IMPLANTABLE ORTHOPAEDIC BEARING--.

Signed and Sealed this
Fifth Day of April, 2011

David J. Kappos
*Director of the United States Patent and Trademark Office*